United States Patent [19]

Pedersen

[11] Patent Number: 5,306,634
[45] Date of Patent: Apr. 26, 1994

[54] SOLUBLE ALDC DERIVATIVE AND USE THEREOF

[75] Inventor: Sven Pedersen, Gentofte, Denmark

[73] Assignee: Novo Nordisk A/S, Bagsvaerd, Denmark

[21] Appl. No.: 976,983

[22] PCT Filed: Aug. 9, 1991

[86] PCT No.: PCT/DK91/00222
§ 371 Date: Feb. 1, 1993
§ 102(e) Date: Feb. 1, 1993

[87] PCT Pub. No.: WO92/03543
PCT Pub. Date: Mar. 5, 1992

[30] Foreign Application Priority Data

Aug. 16, 1990 [DK] Denmark .................. 1949/90

[51] Int. Cl.⁵ .............. G12N 9/88; G12N 9/96; C12C 1/00; C12G 1/00
[52] U.S. Cl. .................. 435/232; 426/12; 435/93; 435/161; 435/188
[58] Field of Search .......... 435/93, 161, 188, 232; 426/11, 12

[56] References Cited

U.S. PATENT DOCUMENTS

| | | | |
|---|---|---|---|
| 4,241,185 | 12/1980 | Stein et al. | 435/188 |
| 4,617,273 | 10/1986 | Olsen et al. | 435/232 |
| 4,708,875 | 11/1987 | Godtfredsen et al. | 426/12 |
| 4,895,802 | 1/1990 | Sone et al. | 435/172.3 |
| 5,043,276 | 8/1991 | Yamano et al. | 435/161 |
| 5,108,925 | 4/1992 | Enari et al. | 435/256 |

FOREIGN PATENT DOCUMENTS 0128714 12/1984 European Pat. Off. .
0131251 1/1985 European Pat. Off. .

OTHER PUBLICATIONS

Baker et al., Biotech. Letts, vol. 10, No. 5, pp. 325-330 (1988).

Primary Examiner—James C. Housel
Assistant Examiner—Robert Carpenter
Attorney, Agent, or Firm—Steve T. Zelson; Karen A. Lowney

[57] ABSTRACT

The ALDC derivative is produced by treating ALDC in an aqueous medium with glutaraldehyde in defined proportions with optional subsequent immobilization. The ALDC derivative which is used in beer fermentation exhibits a satisfactory stability at low pH.

4 Claims, 9 Drawing Sheets

SOLUBLE ALDC DERIVATIVE AND USE THEREOF

The invention comprises a soluble ALDC derivative and a use thereof. ALDC is an abbreviation for acetolactate decarboxylase.

By fermentation of carbohydrate containing substances, e.g. wort or grape juice, various by-products may be formed by processes other than the wanted alcoholic fermentation. Thus, an unwanted by-product is diacetyl.

It appears from EP 46066 that ALDC can be used as an enzyme, which prevents the formation of diacetyl. However, the pH optimum of most naturally occurring ALDC's is around 6, and the activity at pH 3.8–4.7, which is the pH of the fermenting wort, is too low for practical purposes, especially at pH below 4, which is a usual pH of fermenting worts with low malt content. For that reason, the process of preventing the formation of diacetyl from fermenting beer or wine has not yet found its way into the practical industrial production on any larger scale. In EP 46066 it is stated that ALDC may be chemically modified to shift the optimum activity to lower pH values, reference being made to Biochem., vol. 11, No. 22, 1972 (p. 4022–4084). The modification methods mentioned in the Biochem. article comprise growing poly(ornithyl) side chains on chymotrypsin; the Biochem. article thus does not offer any suggestions for modification of ALDC. The prior art modification method for shifting the optimum activity to lower pH values is not suitable for industrial application, and furthermore it is not known, if the poly(ornithyl) method can be transferred from chymotrypsin to ALDC. Finally, it does not appear from the Biochem. article, if the stability at low pH of the prior art modified chymotrypsin is satisfactory.

Thus, the purpose of the invention is the provision of an ALDC derivative which can be used with advantage in industry, and which exhibits a satisfactory stability at low pH.

Surprisingly, it has been found that treatment of ALDC with glutaraldehyde provides a soluble modified ALDC, which in the first place exhibits the wanted pH profile, which in the second place is cheap and easily manufactured, and which in the third place exhibits a satisfactory stability.

Thus, the soluble ALDC derivative according to the invention is characterized by the fact that ALDC in an aqueous medium is treated with glutaraldehyde in a concentration corresponding to between 0.1 and 5 g of glutaraldehyde per g of pure ALDC protein, preferably corresponding to between 0,25 and 2 g of glutaraldehyde per g of pure ALDC protein. It has been found that this ALDC derivative is soluble, if not further treated and that it can be produced in a high activity yield.

In Biotechnology Letters Vol. 10 No. 5 325-330 (1988) it is described that crosslinking of $\beta$-glucosidase with glutaraldehyde provides a derivative with improved thermal stability. In Adv. Biochem. Eng. 12, p. 41–118, 1979, Rolf D. Schmid describes that crosslinking of different enzymes, e.g. papain, glucose oxidase, catalase and uricase, but not ALDC, provides enzyme derivatives with improved thermal stability. Thus, the prior art does not point to glutaraldehyde as an agent which could fulfil the purpose of the invention.

It is to be understood that all ALDC enzymes, i.e. ALDCs produced from any microorganism, can be used according to the invention. Preferred ALDC's are from *Bacillus brevis* and *Bacillus licheniformis*.

Reference can be made to EP 131251, which describes a special inorganic carrier, on which enzymes, e.g. ALDC, are immobilized by adsorption and cross-linking with glutaraldehyde. The invention, in contradistinction thereto, comprises a soluble ALDC derivative exclusively. Also this EP, does not describe the shift of the pH of the pH-activity curve of the ALDC, which is one of the main features of the present invention. Another main feature of the present invention, which is not described in the EP, is the treatment of the ALDC with glutaraldehyde in a defined small concentration.

Also, the invention comprises a use of the soluble ALDC derivative according to the invention in beer fermentation.

A preferred embodiment of the use according to the invention is characterized by the fact that the soluble ALDC derivative is used together with ordinary yeast in a batch fermentation. This is the simplest way of using the soluble ALDC derivative according to the invention.

The invention will be illustrated by means of the following examples. In these examples an ALDC preparation will be used, produced by cultivation of a *Bacillus subtilis* strain containing a gene encoding and expressing the ALDC of *Bacillus brevis* with properties described in DK 149335B.

EXAMPLE 1

100 ml of ALDC solution (batch EDF 212, which is the fermentation liquor centrifugate with an ALDC activity of 1700 ADU/ml) was mixed with 2.5 ml of a 2% glutaraldehyde solution (final glutaraldehyde concentration 0.05% (w/w, corresponding to 0.5 g of glutaraldehyde/g of ALDC). The reaction mixture was cooled with ice for three hours. pH was constantly adjusted to 7.5.

Figure 1:
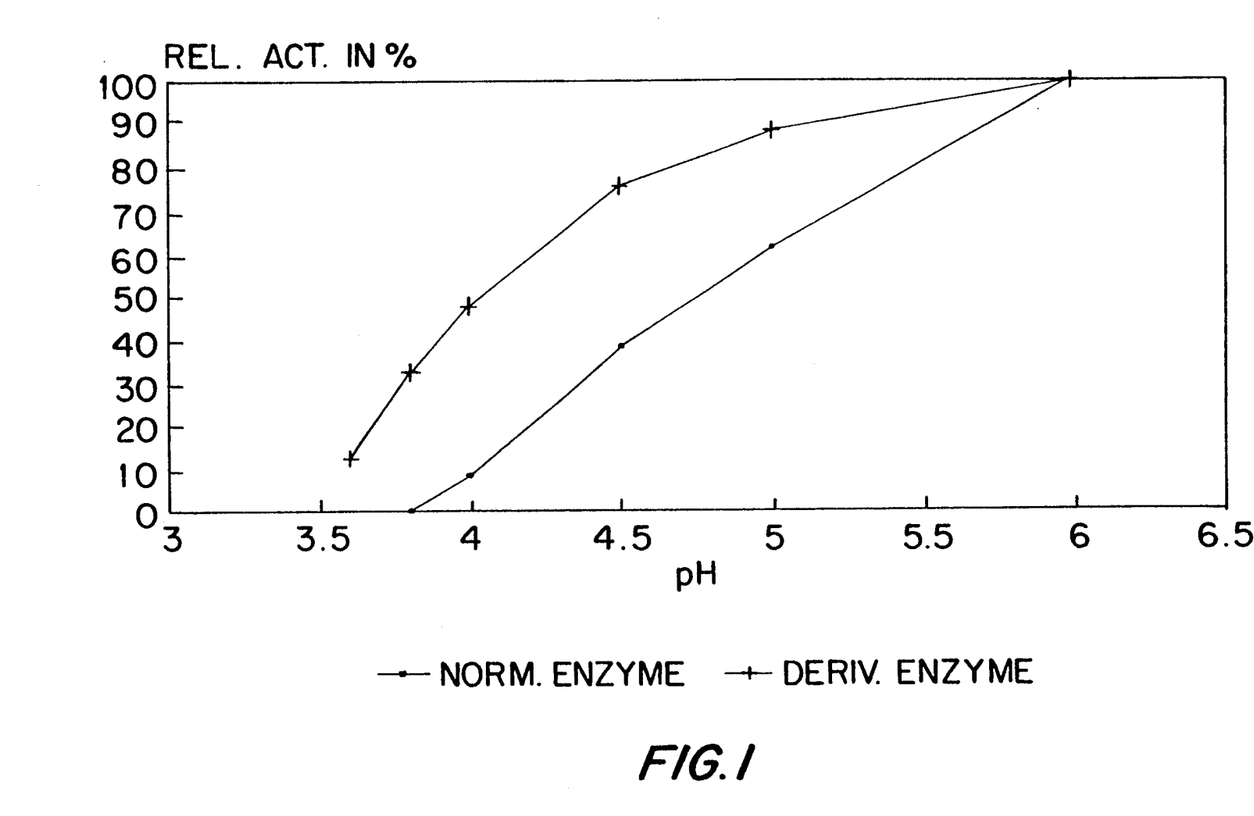
FIG. 1 shows a comparison of the activities of the ALDC derivative of the present invention (derivatized ALDC) and normal ALDC at different pHs.

The ALDC activity (ADU/ml) was measured by Novo Analysis method AF 278/1-GB (available on request from Novo Nordisk A/S, Novo Allé, DK-2880 Bagsvaerd) with pH adjusted in the substrates to values ranging from 3.6 to 6.0. The pH-activity curves are shown in FIG. 1.

Figure 2:
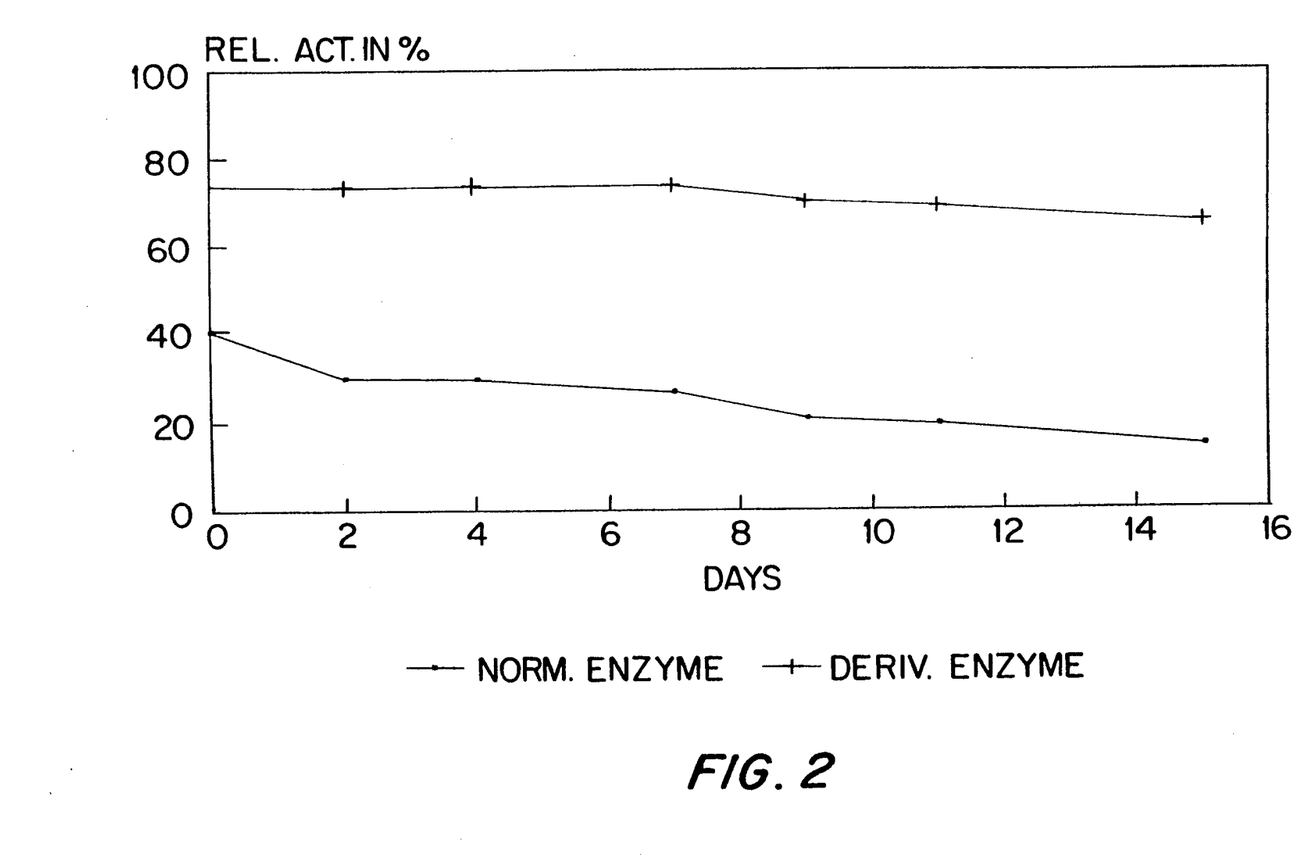
FIG. 2 shows a comparison of the residual activities of derivatized ALDC and normal ALDC after contact with pasteurized beer over a period of several days at pH 4.
Figure 3:
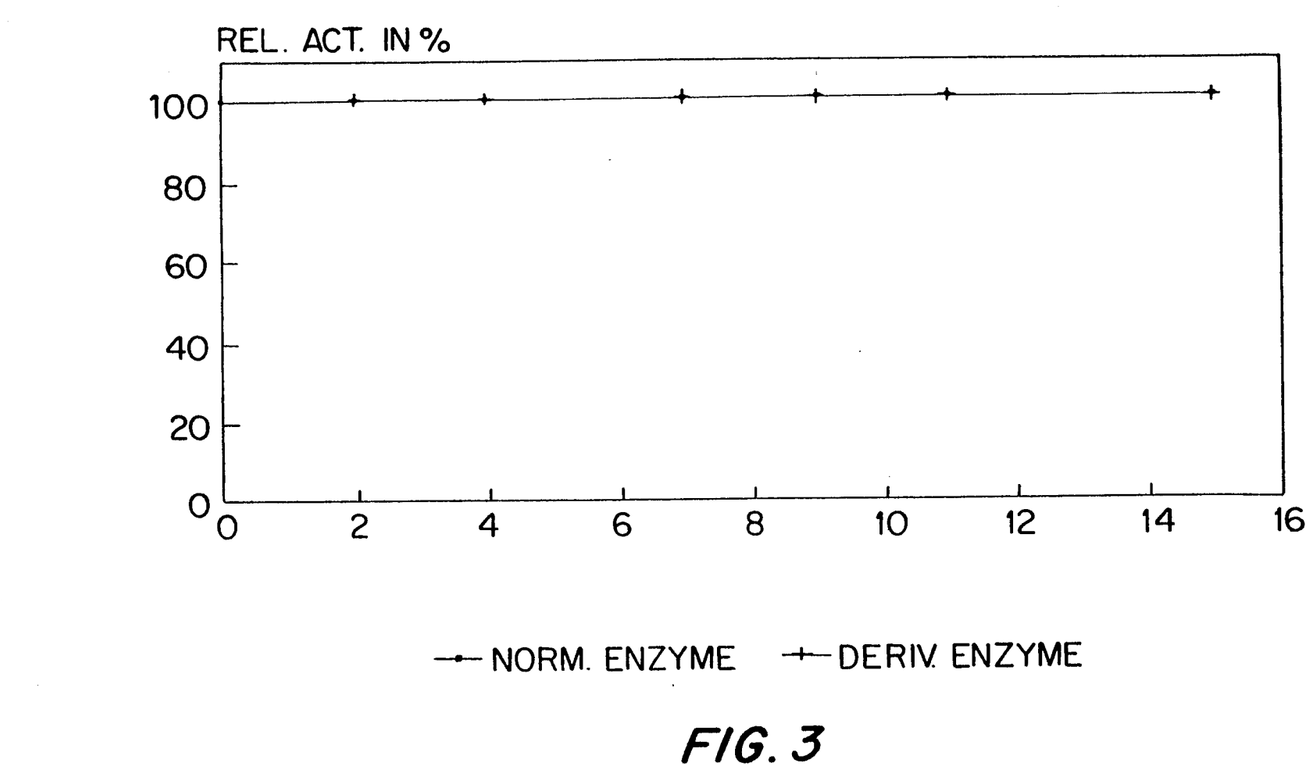
FIG. 3 shows a comparison of the residual activities of derivatized ALDC and normal ALDC after contact with pasteurized beer over a period of several days at pH 6.

The stability of ALDC and the derivatized sample was measured in a normal, pasteurized Danish beer (HOF). 20 ADU was added per ml beer in which pH was adjusted to 4.0 and 6.0, respectively. Samples from the beers were taken each day, and the residual ALDC activity measured at pH 6.0. The results are shown in FIGS. 2 and 3.

It is concluded that treatment with glutaraldehyde improves both the activity and the stability at pH 4.0 of ALDC.

EXAMPLE 2

Testing of Derivatized ALDC in a Traditional Batch Fermentation

ALDC (batch EDF 212, 1700 ADU/ml) (preparation 1) and a glutaraldehyde treated ALDC (preparation 2) prepared as described in Example 1 (1100 ADU/ml) were used.

Figure 4:
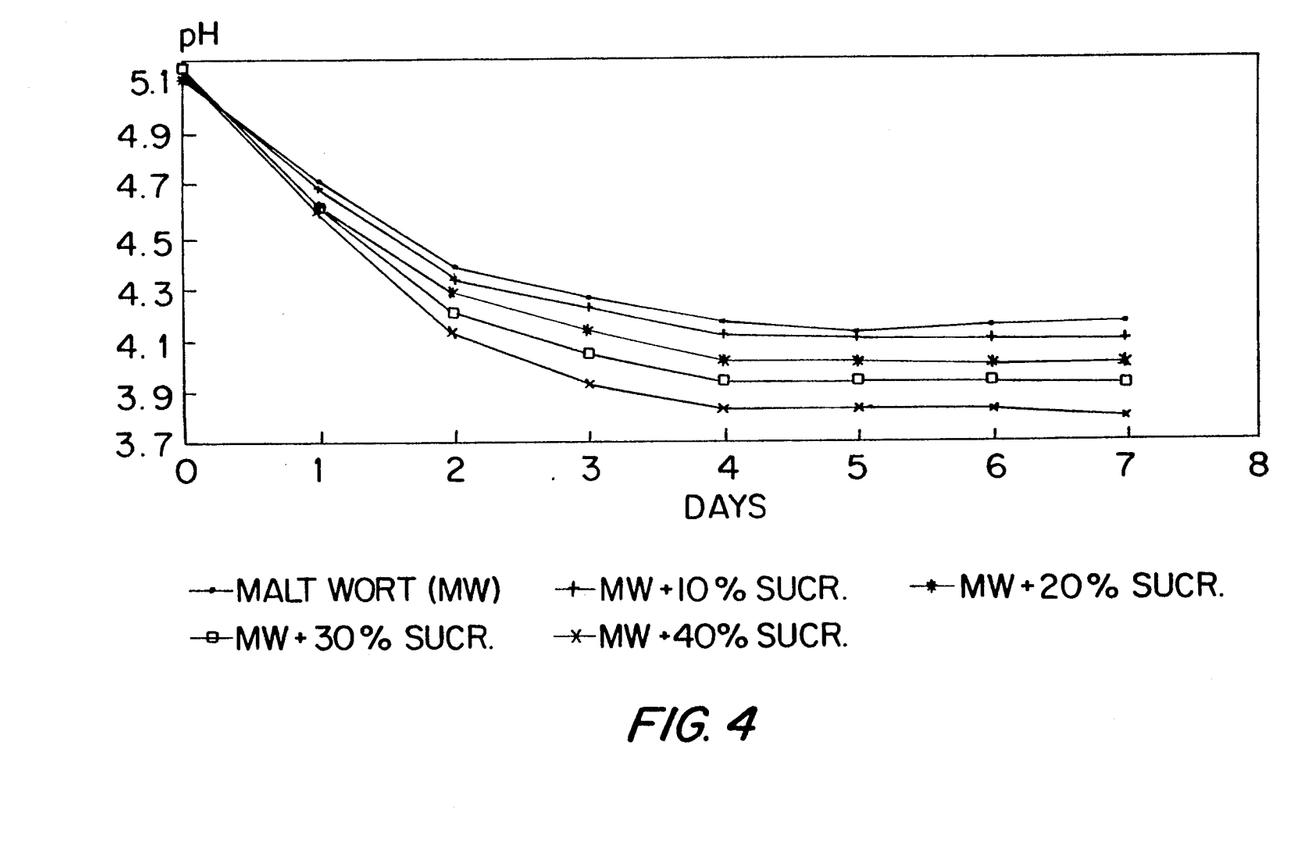
FIG. 4 shows the pattern of pH change in a traditional batch fermentation, using brewery malt wort, with or without varying concentrations of sucrose, over a period of seven days.
Figure 5:
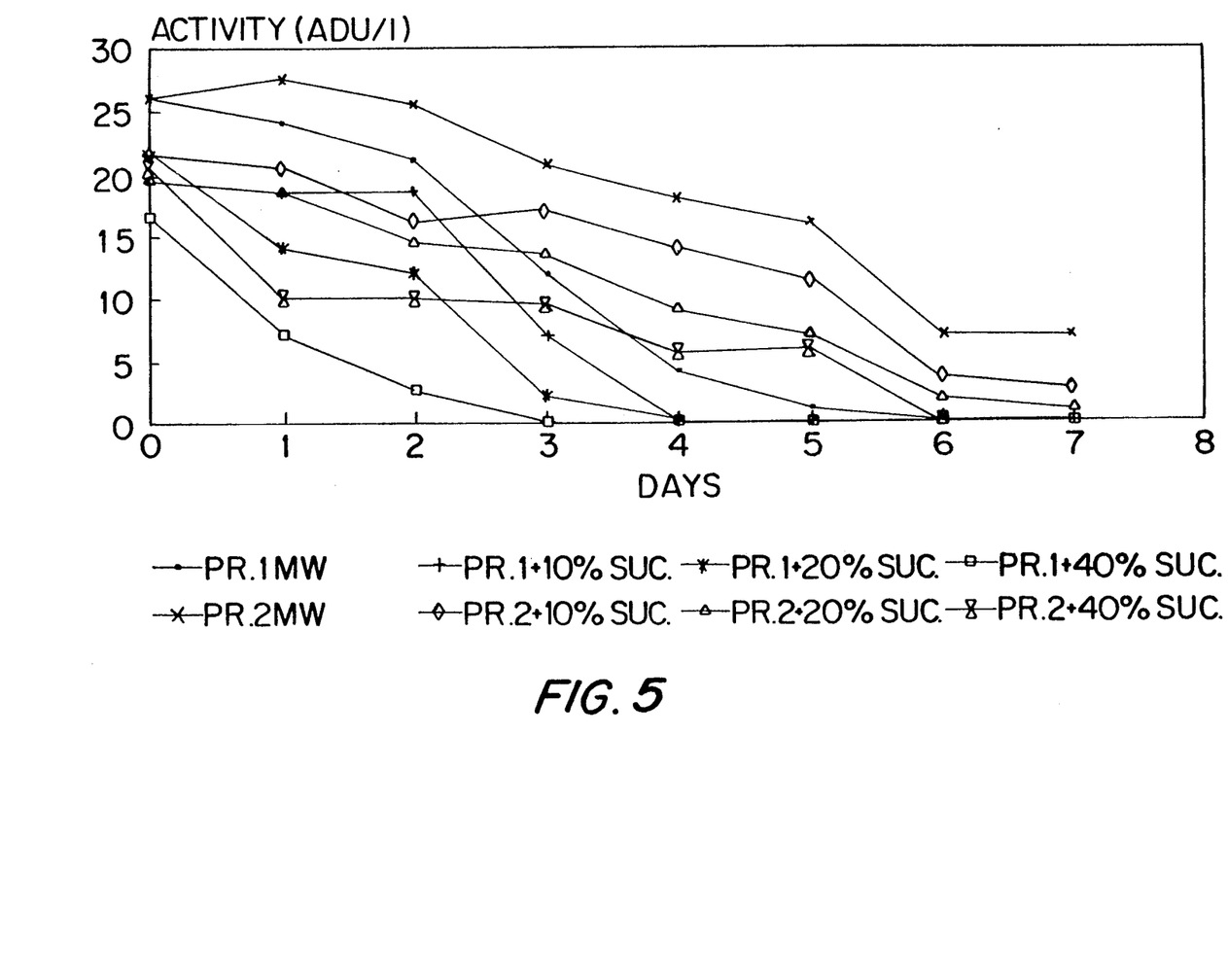
FIG. 5 shows the pattern of residual ALDC activity remaining in a traditional batch fermentation, using brewery malt wort, with or without varying concentrations of sucrose, over a period of seven days. Pr.1=normal ALDC preparation; Pr.2=derivatized ALDC.
Figure 6:
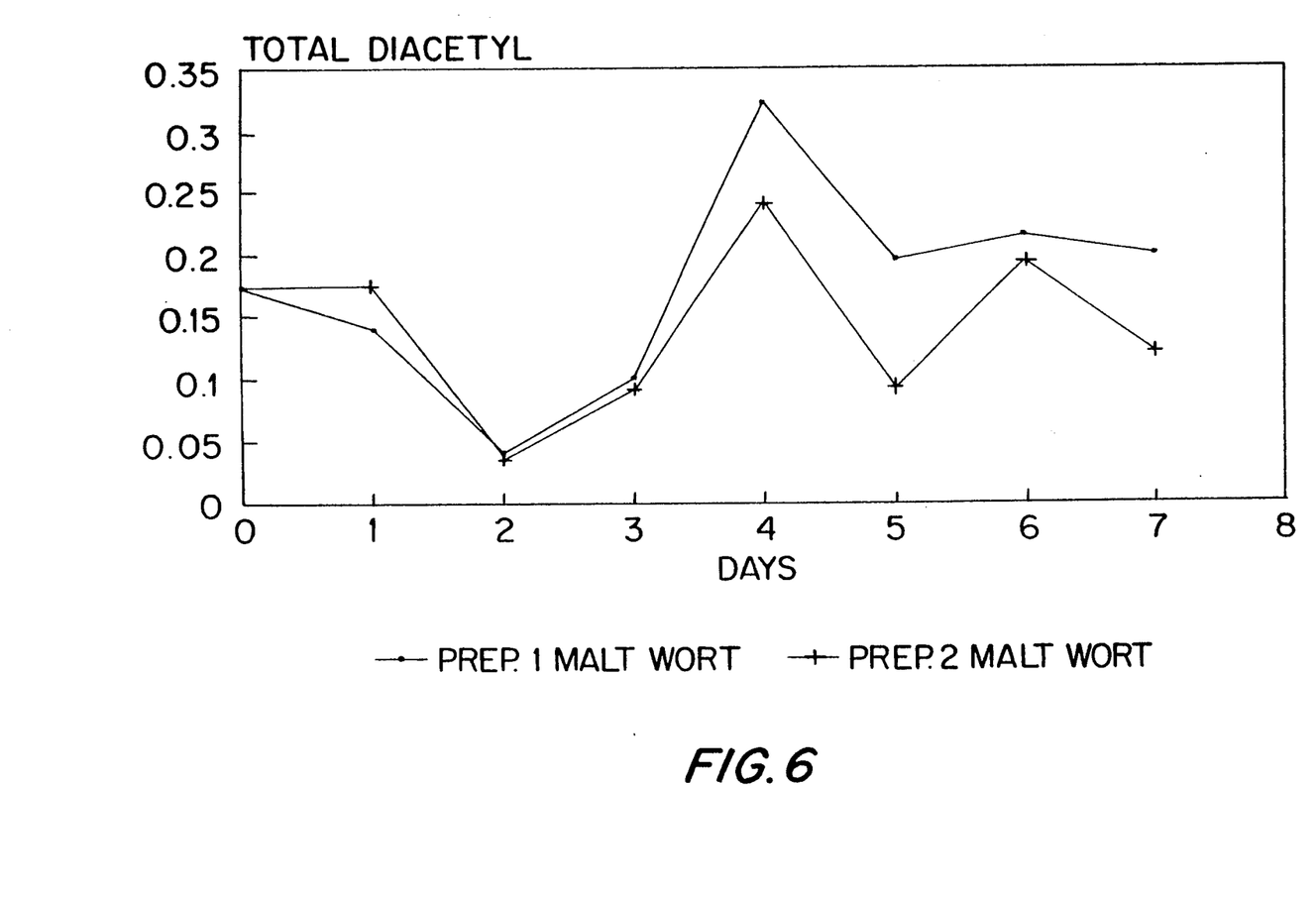
FIG. 6 shows a comparison of the change in total diacetyl in a traditional batch fermentation, using derivatized ALDC or normal ALDC with brewery malt wort alone, over a period of seven days. Prep.1=normal ALDC preparation; Prep.2=derivatized ALDC.
Figure 7:
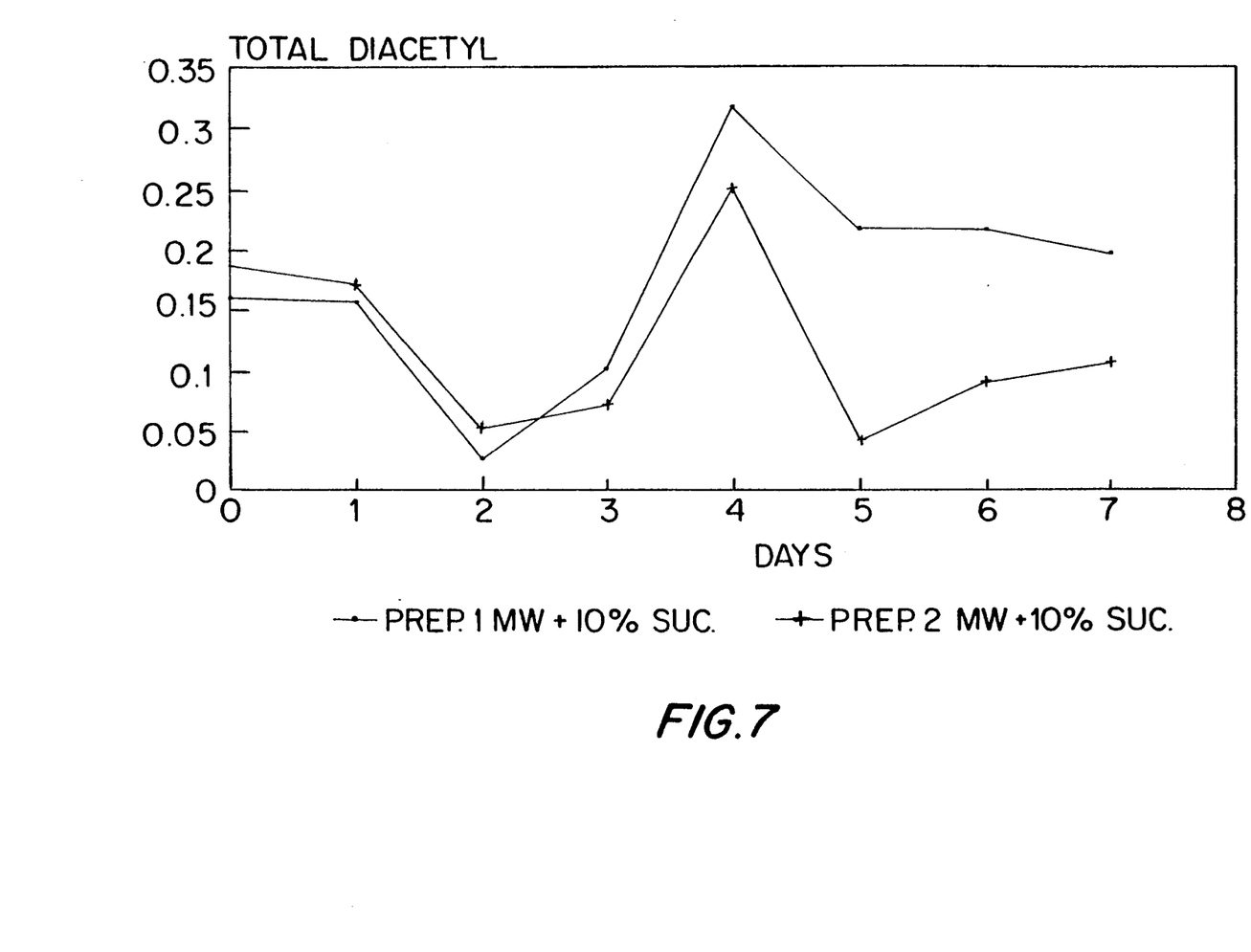
FIG. 7 shows a comparison of the change in total diacetyl in a traditional batch fermentation, using derivatized ALDC or normal ALDC with brewery malt wort plus 10% sucrose, over a period of seven days. Prep.1=normal ALDC preparation; Prep.2-=derivatized ALDC.
Figure 8:
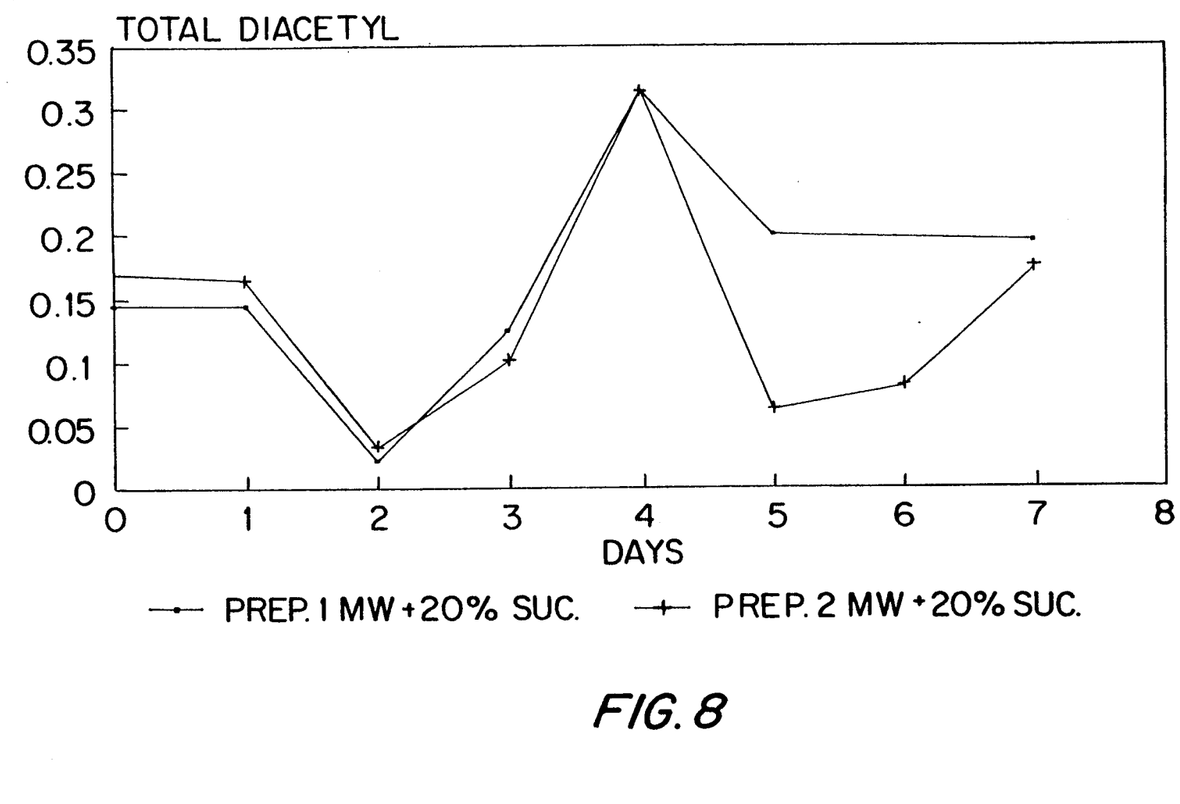
FIG. 8 shows a comparison of the change in total diacetyl in a traditional batch fermentation, using derivatized ALDC or normal ALDC with brewery malt wort plus 20% sucrose, over a period of seven days. Prep.1=normal ALDC preparation; Prep.2-=derivatized ALDC.
Figure 9:
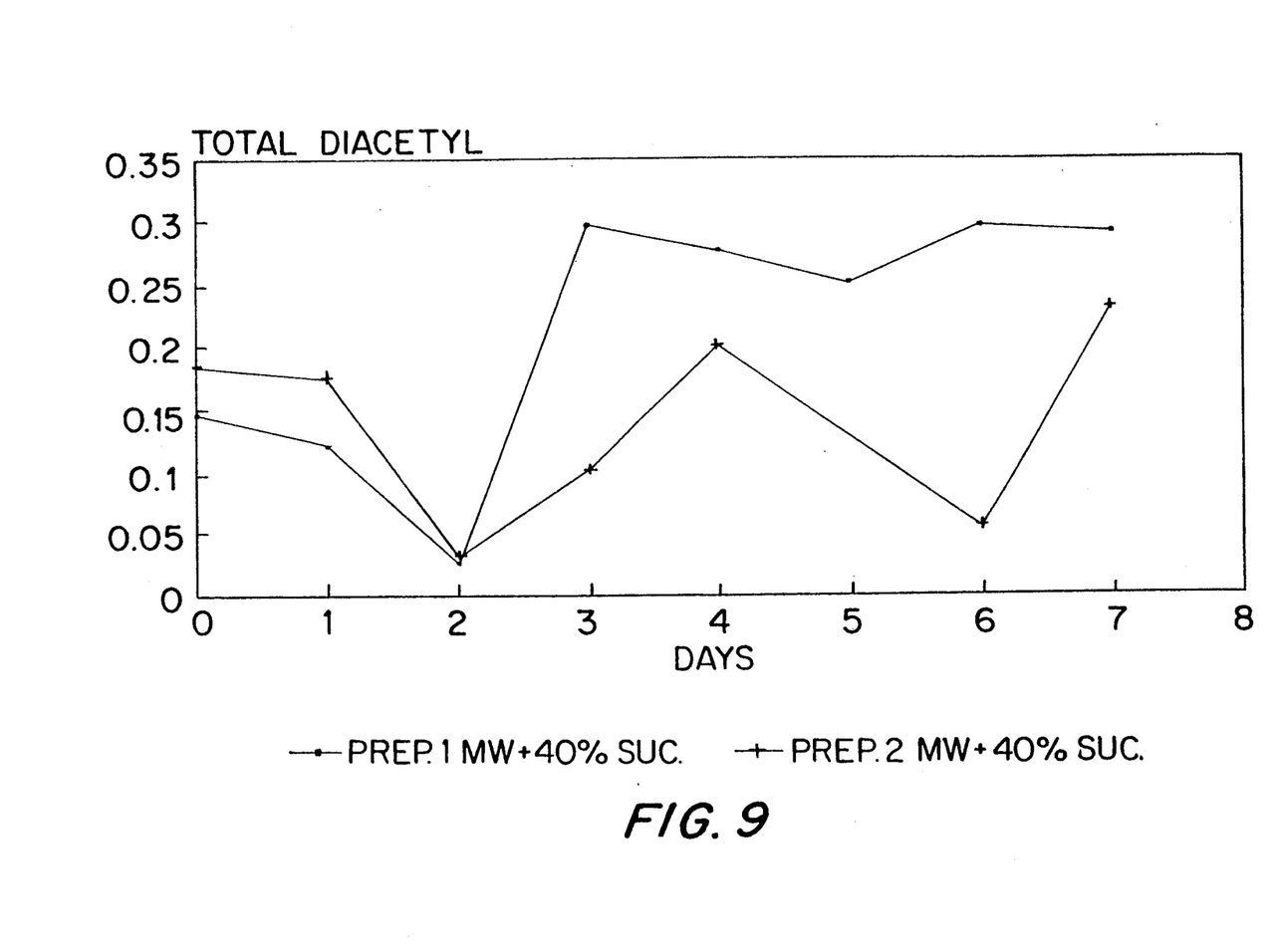
FIG. 9 shows a comparison of the change in total diacetyl in a traditional batch fermentation, using derivatized ALDC or normal ALDC with brewery malt wort plus 40% sucrose, over a period of seven days. Prep.1=normal ALDC preparation; Prep.2-=derivatized ALDC.

The fermentations were carried out with brewery malt wort (FAXE) and the same wort with added amounts (10, 20, 30 and 40% w/w) of adjunct (sucrose). 2.5 g of yeast was added per liter of wort. ALDC was added together with the yeast (46 ADU per liter). The fermentations were carried out at 12° C. and lasted for 7 days. pH (FIG. 4), ALDC residual activity (FIG. 5) and total diacetyl ($\alpha$-acetolactid acid + diacetyl) (FIGS. 6–9) were measured each day.

The results show that the reduction of total diacetyl is larger when the derivatized ALDC (prep. 2) is used than when untreated ALDC is used, and that the derivatized preparation is more stable.

I claim:

1. A soluble derivative of acetolactate decarboxylase (ALDC), wherein the derivative is obtained by treatment of ALDC in an aqueous medium with glutaraldehyde, in a concentration of between 0.1 and 5 g of glutaraldehyde per g of pure ALDC protein in the medium.

2. The derivative of claim 1, wherein the glutaraldehyde is in a concentration of between 0.25 and 2 g of glutaraldehyde per g of pure ALDC protein.

3. A method for removing diacetyl from a beer fermentation liquor comprising contacting the fermentation liquor with a soluble ALDC derivative obtained by treatment of ALDC in an aqueous medium with glutaraldehyde in a concentration of between 0.1 and 5 g of glutaraldehyde per g of pure ALDC protein in the medium.

4. The method of claim 3, which is conducted with non-immobilized yeast in a batch fermentation.

* * * * *